(12) United States Patent
Hosted, Jr. et al.

(10) Patent No.: US 6,569,668 B2
(45) Date of Patent: May 27, 2003

(54) **ISOLATED NUCLEIC ACIDS FROM *MICROMONOSPORA ROSARIA* PLASMID PMR2 AND VECTORS MADE THEREFROM**

(75) Inventors: Thomas J. Hosted, Jr., Summit, NJ (US); Ann C. Horan, Summit, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/821,167

(22) Filed: Mar. 29, 2001

(65) Prior Publication Data

US 2002/0015989 A1 Feb. 7, 2002

Related U.S. Application Data

(60) Provisional application No. 60/194,461, filed on Apr. 4, 2000.

(51) Int. Cl.[7] .......................... C12N 1/20; C12N 15/00; C07H 21/02; C07H 21/04
(52) U.S. Cl. ................ 435/252.3; 435/320.1; 536/23.1; 536/23.7
(58) Field of Search ...................... 530/350; 435/320.1, 435/183, 252.3; 536/23.1, 23.7

(56) References Cited

U.S. PATENT DOCUMENTS 5,741,675 A * 4/1998 Freldmann et al.

FOREIGN PATENT DOCUMENTS

| EP | 0138337 A | 4/1985 |
|---|---|---|
| EP | 0344767 | 12/1989 |
| JP | 60047684 A | 3/1985 |
| JP | 01304887 A | 12/1989 |

OTHER PUBLICATIONS

Brown et al. (J Bact 1990 vol. 172(4) pp 1877–88).*
Katz et al. (Mol Gen Genet 1991 227(1) pp 155–9).*
International Search Report for International Patent Application No. PCT/US01/10321.
Mazodier, et al., (1989) J. Bacteriology 171 (6): 3583–3585.

* cited by examiner

*Primary Examiner*—Mark Navarro

(57) ABSTRACT

Plasmid genes from *Micromonospora rosaria* pMR2 have been isolated, cloned, sequenced and functionally identified. These genes have been used to create vectors which can be used to express actinomycete genes, manipulate metabolic pathways and produce useful gene products such as hybrid antibiotics.

16 Claims, 3 Drawing Sheets

SCEMATIC REPRESENTATION OF THE *MICROMONOSPORA ROSARIA* pMR2 PLASMID. OPEN READING FRAMES ARE INDICATED BY ARROWS. ds-ORIGIN OF REPLICATION AND attP SITE ARE INDICATED BY SOLID BARS.

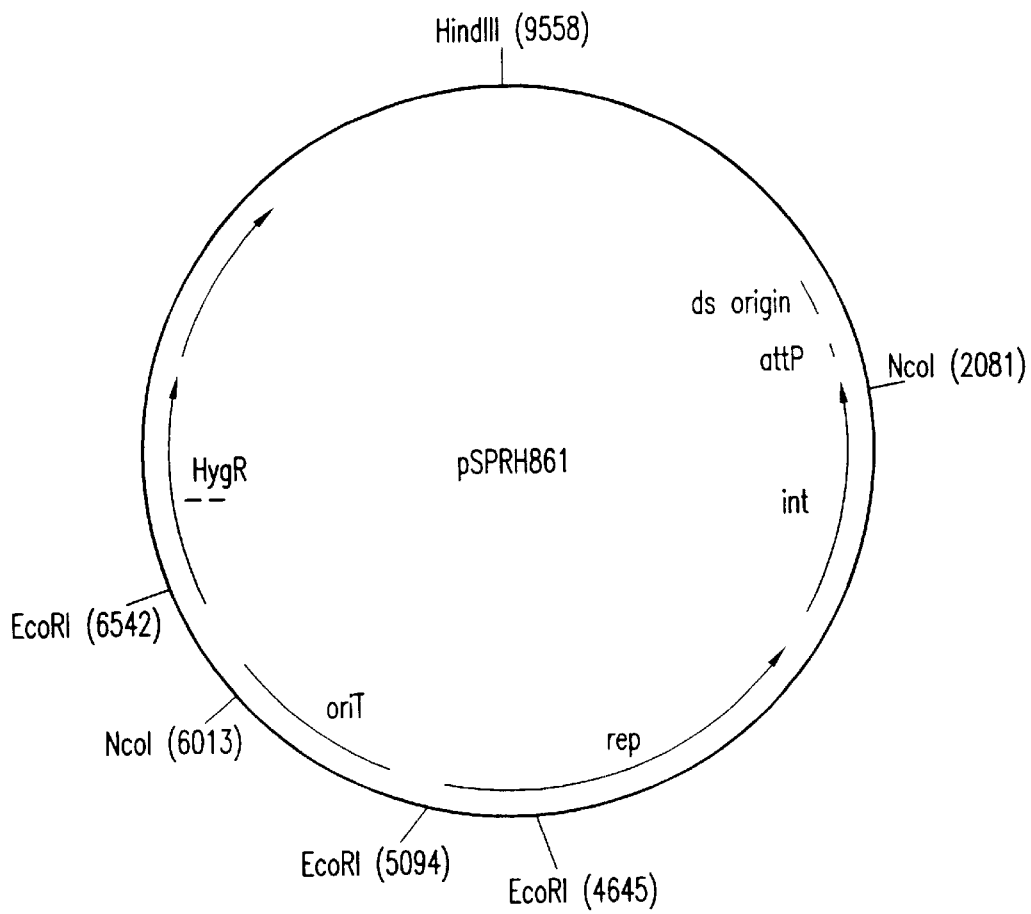

*E. COLI-MICROMONOSPORA* SHUTTLE VECTOR pSPRH861 pSPRH861 – pSPRH826b BACKBONE CONTAINING A 5.4 kb FRAGMENT FROM THE *M. ROSARIA* NRRL3718 pMR2 PLASMID. REP, PLASMID REPLICATION PROTEIN; INT, INTEGRATE; attP, ATTACHMENT SITE; ds-ORIGIN, DOUBLE-STRANDED ORIGIN OF REPLICATION; β-LACTAMASE, AMPICILLIN RESISTANCE; HygR, HYGROMYCIN RESISTANCE; oriT, RK2 ORIGIN OF TRANSFER FOR CONJUGATION. RESTRICTION SITES ARE INDICATED.

FIG.2 pSPRH826b PLASMID. β-LACTAMASE, AMPICILLIN RESISTANCE; HYGROMYCIN RESISTANCE; oriT, RTK2 ORIGIN OF TRANSFER FOR CONJUGATION. RESTRICTION SITES ARE INDICATED.

ISOLATED NUCLEIC ACIDS FROM *MICROMONOSPORA ROSARIA* PLASMID PMR2 AND VECTORS MADE THEREFROM

This application claims the benefit of U.S. Provisional Application No. 60/194,461 filed Apr. 4, 2000.

FIELD OF THE INVENTION

The present invention relates generally to isolated nucleic acids and the creation of vectors incorporating the same for the study and expression of genes in actinomycetes. The invention more particularly relates to novel genes isolated from a Micromonospora plasmid which can be used in the construction of vectors for the study and expression of genes and manipulation of metabolic pathways in actinomycete hosts.

BACKGROUND

Actinomycetes are branched filamentous Gram-positive bacteria. Streptomyces, Micromonospora, Nocardia, Actinoplanes, Saccharopolyspora, Actinomadura, Thermomonospora, Microbispora, Streptosporangium and others all represent genera of the Actinomycetes (Atlas of Actinomycetes, Asakura Publishing Co., Ltd 1996). Actinomycetes are very important industrially because they produce a variety of secondary metabolites such as antibiotics, herbicides, anticancer agents, antihelmintics, and anabolic agents (Demain., Appl. Microbiol and Biotechnology., 1999, 52:455–463). Antibiotics are a large and complex group of chemical substances which exert deleterious effects on other organisms, many of which organisms are harmful to humans. Thus, antibiotics are particularly important secondary metabolites to study and produce. This is especially true because many pathogens can develop antibiotic resistance to known antibiotics.

Given the actinomycetes' proclivity for producing secondary metabolites such as antibiotics, it is especially advantageous to develop new tools such as vectors, promoters and the like to allow actinomycetes to be easily genetically manipulated. These tools would make it possible to control the levels of expression of genes encoding for secondary metabolites and also would make it possible to prepare derivatives or intermediates of these metabolites. In addition, the development of new vectors utilizing novel genes would make it possible to program microorganisms such as actinomycetes to produce recombinant products such as hybrid antibiotics via genetic engineering techniques.

In particular, it would be useful to construct replication, *Escherichia coli*-actinomycete shuttle, conjugal and integrating vectors which can be used to express genes in actinomycetes, for complementation experiments and heterologous gene expression.

Integrating vectors can be created which allow efficient integration of genes into a transformed host's chromosome rather than replicating autonomously. They are particularly useful in transforming actinomycetes because of their high transformation rates, site specific integrative capacity and stable maintenance in host chromosomes without antibiotic selection. Vectors have been developed for use in actinomycetes that contain att/int functions for site specific integration of plasmid DNA. The two systems available make use of the att/int functions of bacteriophage phiC31 (U.S. Pat. No. 5,190,870) and plasmid pSAM2 (U.S. Pat. No. 5,741,675). However, there is a need for additional vectors with att/int functions for site-specific integration in *M. carbonacea* and similar organisms.

*E. coli*-actinomycete shuttle vectors can be created which will allow many traditional and facile molecular and genetic manipulations to be performed in *E. coli*. Plasmids developed in *E. coli* can then be introduced into actinomycetes to study their effects.

The ability to develop actinomycete conjugation vectors would allow intramycelial transfer which enables the transfer of plasmids between different phylogenetic classes of actinomycetes.

The present inventors have responded to the above needs and have isolated plasmid genes from *Micromonospora rosaria,* a species of actinomycete, in order to create vectors which can be used to express actinomycete genes, manipulate secondary metabolic pathways and create new metabolic products such as hybrid antibiotics. In addition, the isolated genes can be used to create replicating, *E. coli*-actinomycete shuttle, integrating, and intermycelial and intramycelial conjugation vectors for use in actinomycetes.

SUMMARY OF THE INVENTION

The present invention advantageously provides the polynucleotide sequences for the genes encoding the proteins and DNA regions required for the replication, transfer and integration of the *M. rosaria* pMR2 plasmid. As a result, the present invention provides the information needed to construct novel replicating, shuttle, integrating and conjugation vectors derived from the *M. rosaria* pMR2 plasmid. In addition, the invention provides hosts transformed with these novel vectors.

In one embodiment, the present invention provides isolated polynucleotides comprising sequences which are at least about ninety percent homologous to the nucleotide sequences set forth in SEQ ID NOS: 2–15. In a preferred embodiment, the present invention provides isolated polynucleotides comprising sequences set forth in SEQ ID NOS: 2–15. These isolated polynucleotides encode novel genes and DNA sequences involved in plasmid replication, integration, excision, and intermycelial and intramycelial conjugation. In preferred embodiments, these isolated sequences encode a site-specific integrase, an excisionase, an attachment site for plasmid integration, inter- and intramycelial transfer genes, origin of replication, and plasmid regulatory proteins.

In another embodiment, the present invention provides recombinant vectors comprising a sequence having at least about ninety percent homology to a nucleotide sequence selected from the group consisting of SEQ ID NOS: 2–15. In a preferred embodiment, the invention provides recombinant vectors comprising one or more of SEQ ID NOS: 2–15. In an especially preferred embodiment, the recombinant vector is an integration vector capable of integrating into the chromosome of the host cell. In yet another preferred embodiment, the recombinant vector is a vector capable of inter- and intramycelial conjugation in actinomycetes. In still another preferred embodiment, the recombinant vector is capable of replicating in both *E. coli* and actinomycete species.

In yet another embodiment, the present invention provides host cells comprising the vectors of the instant invention. In a preferred embodiment, the host cells are bacterial. In an especially preferred embodiment, the host cells are *Micromonospora carbonacea, Micromonospora halophitica,* and/or *Streptomyces lividans.*

In a final embodiment, the present invention provides an isolated polynucleotide comprising a sequence having at least about ninety percent homology to the sequence set forth in SEQ ID NO:1. Preferably, the polynucleotide comprises a sequence identical or nearly identical to the sequence set forth in SEQ ID NO: 1.

These and other aspects of the invention are better understood by reference to the following Detailed Description and Examples.

BRIEF DESCRIPTION OF THE DRAWINGS

FIG. 2 Map of the *E. coli*-actinomycete shuttle vector pSPRH861.

DETAILED DESCRIPTION OF THE INVENTION

Figure 1:
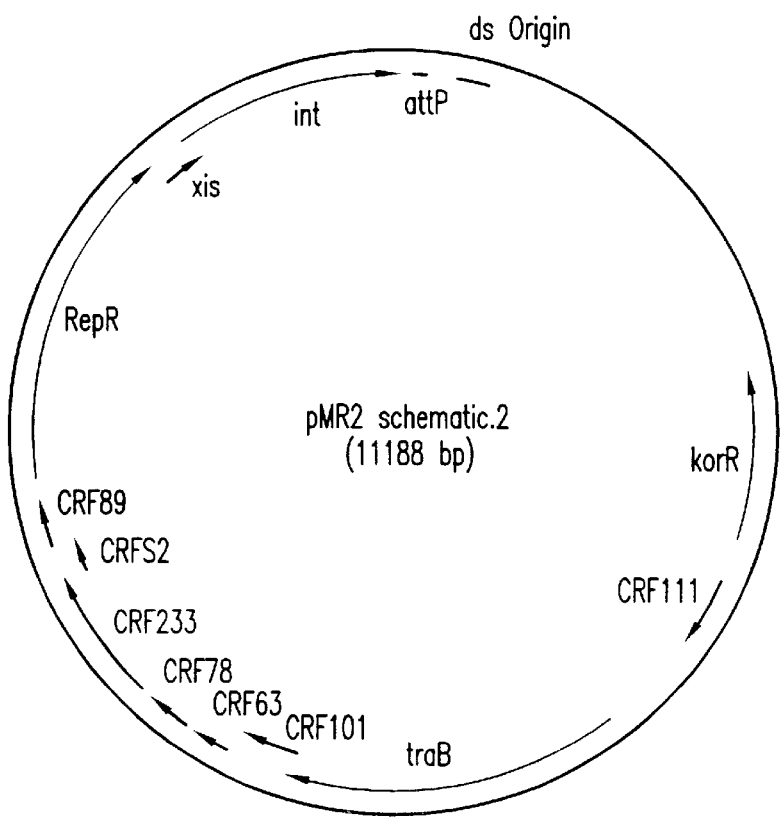
FIG. 1 Map of plasmid pMR2 indicating novel plasmid genes and DNA regions which were isolated, sequenced and functionally identified.

The present invention relates to nucleic acids isolated from plasmid pMR2 which was isolated from *Micromonospora rosaria*. In addition, the invention relates to vector constructs made utilizing these nucleic acids. These vectors can be used to express actinomycete genes and manipulate secondary metabolic pathways in actinomycetes for their study and for the expression of useful products.

Before describing the invention in detail, the following definitions are provided to aid in an understanding of the specification and claims:

"Nucleic acid" or "polypeptide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

An "open reading frame" (ORF) as used herein is a region of a polynucleotide sequence that encodes a polypeptide; this region may represent a portion of a coding sequence or comprise a total coding sequence for the polypeptide.

A "coding sequence" or a "protein-coding sequence" is a polynucleotide sequence capable of being transcribed into mRNA and/or capable of being translated into a polypeptide. The boundaries of the coding sequence are typically determined by a translation start codon at the 5'-terminus and a translation stop codon at the 3'-terminus.

A "complement" of a nucleic acid sequence as used herein refers to the "antisense" sequence that participates in Watson-Crick base-pairing with the original sequence.

An "isolated" nucleic acid or polypeptide as used herein refers to a nucleic acid that is removed from its original environment such as, for example, from *Micromonospora-cea rosaria* plasmid pMR2. An isolated nucleic acid or polypeptide contains less than about 50%, preferably less than about 75%, and most preferably less than about 90%, of the cellular components with which it was originally associated.

A "*M. rosaria*-derived" nucleic acid or polypeptide sequence may or may not be present in other bacterial species, and may or may not be present in all *M. rosaria* strains. This term is intended to refer to the source from which the sequence was originally isolated. An *M. rosaria* plasmid-derived polypeptide, as used herein, may be used to search for homologous proteins in other species of bacteria or in eukaryotic organisms such as fungi and humans, etc.

Nucleic acids are "hybridizable" to each other when at least one strand of nucleic acid can anneal to another nucleic acid strand under defined stringency conditions. Stringency of hybridization is determined, by the temperature at which hybridization and/or washing is performed and the ionic strength and polarity of the hybridization and washing solutions, as well as other parameters. Hybridization requires that the two nucleic acids contain substantially complementary sequences; depending on the stringency of hybridization, however, mismatches may be tolerated. The appropriate stringency for hybridizing nucleic acids depends on the length of the nucleic acids and the degree of complementarity, variables well known in the art.

"Gene" refers to a DNA sequence that encodes through its template or messenger RNA a sequence of amino acids characteristic of a specific peptide, polypeptide or protein. The term "gene" as used herein with reference to genomic DNA includes intervening, non-coding regions, as well as regulatory regions, and can include 5' and 3' ends.

"Gene sequence" refers to a DNA molecule, including both a DNA molecule which contains a non-transcribed or non-translated sequence. The term is also intended to include any combination of gene(s), gene fragment(s), non-transcribed sequence(s) or non-translated sequence(s) which are present on the same DNA molecule.

"Homologous nucleic acid sequences" are those which when aligned and compared exhibit significant similarities. Standards for homology in nucleic acids are either measures for homology generally used in the art by sequence comparison or based upon hybridization conditions, which are described in greater detail below. Nucleotide sequence homology is observed when there is identity in nucleotide residues in two sequences (or in their complementary strands) when optimally aligned to account for nucleotide insertions or deletions. Substantial homology also exists when one sequence will hybridize under selective hybridization conditions to another. Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, e.g., Kanehisa, *Nucleic Acids Res.* 12:203 (1984).

The nucleotide sequences of the present invention may be derived from a variety of sources including DNA, cDNA, synthetic DNA, synthetic RNA or combinations thereof Such sequences may comprise genomic DNA which may or may not include naturally occurring introns. Moreover, such genomic DNA may be obtained in association with promoter regions or poly (A) sequences. The sequences, genomic DNA or cDNA may be obtained in any of several ways. Genomic DNA can be extracted and purified from suitable cells by means well known in the art. Alternatively, mRNA can be isolated from a cell and used to produce cDNA by reverse transcription or other means.

"cDNA" refers to complementary or copy DNA produced from an RNA template by the action of RNA-dependent DNA polymerase (reverse transcriptase). Thus, a "cDNA clone" means a duplex DNA sequence complementary to an RNA molecule of interest, carried in a cloning vector or PCR amplified. This term includes genes from which the intervening sequences have been removed.

"Recombinant DNA" means a molecule that has been recombined by in vitro splicing of cDNA or a genomic DNA sequence.

"Cloning" refers to the use of in vitro recombination techniques to insert a particular gene or other DNA sequence into a vector molecule. In order to successfully clone a desired gene, it is necessary to use methods for generating DNA fragments, for joining the fragments to vector molecules, for introducing the composite DNA molecule into a host cell in which it can replicate, and for selecting the clone having the target gene from amongst the recipient host cells.

"Host" includes prokaryotes and eukaryotes. The term includes an organism or cell that is the recipient of a replicable expression vehicle.

A "site-specific att/int function" refers to an integrase protein and an attP site such as disclosed in (SEQ ID NOS:15, 2) that permits site-specific integration of a vector into a corresponding attB site located on the actinomycete chromosome.

An "integrating vector" is a vector capable of site-specific integration into a bacterial chromosome attB site.

An "insertion vector" is a vector that can insert by homologous recombination into a bacterial chromosome.

A "conjugation vector" is a vector capable of being transferred from one bacteria to another by conjugation.

A "shuttle vector" is a vector capable of replication in E. coli and a second bacterial strain such as an actinomycete.

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, protein extractions with phenol or phemnol/chloroform, ethanol or isopropanol precipitation of DNA in a saline medium, transformation in Escherichia coli, and the like, are well known to a person skilled in the art and are amply described in the literature. Maniatis T., et al., "Molecular Cloning, a Laboratory Manual," Cold Spring Harbor Laboratory, Cold Spring Harbor, N.Y., 1982; Ausubel F. M., et al., (eds), "Current Protocols in Molecular Biology," John Wiley & sons, New York 1987.

Protocols have been developed to genetically manipulate actinomycete genomes and biosynthetic pathways. These include the construction of E. coli-actinomycete shuttle vectors, gene replacement systems, transformation protocols, transposing mutagenesis, insertional mutagenesis, integration systems and heterologous host expression. These techniques are reviewed in numerous articles (Baltz et al., Trends Microbiol., 1998, 2:76–83, Hopwood et al., Genetic Manipulation of Streptomyces: A Laboratory Manual, 1985; Wohlleben et al., Acta Microbiol. Immunol. Hung, 1994, 41:381–9[Review]).

The development of vectors for the genetic manipulation of actinomycetes began with the observation of plasmids in actinomycetes and the development of a transformation protocol of actinomycete protoplasts using polyethylene glycol (Bibb et al., Nature, 1980, 284:526–31). Many standard molecular techniques for Streptomyces were developed by Hopwood for Streptomyces coelicolor and Streptomyces lividans (Hopwood et al., Genetic Manipulation of Streptomyces: A Laboratory Manual, 1985). These techniques have been adapted and expanded to other actinomycetes.

Vectors incorporating antibiotic-resistance markers Apramycin (AmR), Thiostrepton (ThR), and Spectinomycin (SpR), that function in Streptomyces and other features have allowed the development of vectors for (a) integration via homologous recombination between cloned DNA and the Streptomyces spp. chromosome, (b) E. coli-actinomycete shuttle vectors, and (c) site-specific integration at the bacteriophage phiC31 attachment (att) site or pSAM2 attachment site, and (d) gene replacement vectors. Homologous recombination between the cloned DNA and the chromosome can be used to make insertional knockouts of specific genes. E. coli-actinomycete shuttle vectors can be used to introduce copies of genes into actinomycetes. Site-specific integration plasmids can be used to introduce heterologous genes into the actinomycete chromosome for complementation, expression studies and production of hybrid secondary metabolites.

Many actinomycetes contain restriction systems that limit the ability to transform organisms by protoplast transformation. More recent gene transfer procedures have been developed for introducing DNA into Streptomycetes by conjugation from E. coli. This employs a simple mating procedure for the conjugal transfer of vectors from E. coli to Streptomyces species that involves plating of the donor strain and either germinated spores or mycelial fragments of the recipient strain. Conjugal plasmids contain the 760-bp oriT fragment from the IncP plasmid, RK2 and are transferred by supplying transfer functions in trans by the E. coli donor strain. Other recent developments that increase the frequency of recombination of non replicating plasmids into the recipient actinomycete chromosome include transformation of non-replicating plasmids into protoplasts using denatured plasmid DNA (Oh and Chater, J. Bacteriol., 1997, 179:1227) and conjugation of non-replicating plasmids from a methyl minus strain of E. coli (Smith et al., FEMS Microbiol. Lett., 1997, 155:2239).

Various strategies have been used to obtain gene replacements in Streptomycetes, for the construction of mutations and the modification of biosynthetic pathways (Baltz et al., 1998, supra; Hopwood et al., supra; Wohllenben et al., 1994, supra; Baltz and Hosted, TIBTECH, 1996, 14:245; Baltz, Curr. Op. Biotech., 1990, 1:1220). These methods have typically employed a two or three step procedure that results in allelic exchange. Initial crossover events between a non-integrating phage, non-replicating plasmid, or temperature sensitive plasmid and the Streptomycete chromosome are selected for by antibiotic resistance. Subsequent recombination events that result in gene replacement can be detected by screening the progeny of the initial recombinants by PCR analysis, Southern analysis, appearance of an expected phenotype or screening for the loss of a resistance marker which had previously been exchanged into the loci to be replaced. The last of these methods has been employed by Khosla et al., Mol. Microbiol., 1992, 6:323749; Khosla et al., J. Bacteriol., 1993, 175:2197204, to successfully modify the polyketide biosynthetic route of S. coelicolor. The strategy employed by Khosla et al., 1992, supra, also has the advantage of allowing placement of non-selectable and phenotypically silent alleles into chosen positions of the chromosome. Donadio et al., Proc. Natl. Acad. Sci. U.S.A., 1993, 90:711923 has also successfully reprogrammed the erythromycin pathway of Saccharopolyspora erythrae by gene replacement.

Non-replicating plasmids for gene replacement were initially utilized by Hilleman et al., Nucleic Acids Res., 1991, 19:72731, who used a derivative of pDH5 to construct mutations in the phosphinothricin tripeptide biosynthetic pathway of S. hygroscopicus. Plasmid-insertion events were obtained by thiostrepton selection, subsequent screening of the primary recombinants indicated that 4 of 100 isolates had undergone a double-crossover gene replacement.

Use of counterselectable or negative selection markers such as rpsL (confers streptomycin sensitivity) or sacB (confers sucrose sensitivity) have been widely employed in other microorganisms for selection of recombination that results in gene replacement. In *S. coelicolor*, Buttner utilized glk as a counterselectable marker in att minus phiC31 phage to select for recombination events to construct gene replacement mutants of three *S. coelicolor* RNA polymerase sigma factors (Buttner et al., J. Bacteriol., 1990, 172:336778). Hosted has developed a gene replacement system utilizing the rpsL gene for counterselection (Hosted and Baltz, J. Bacteirol., 1997, 179:1806).

The construction of recombinant actinomycete strains to produce hybrid secondary metabolites has been accomplished (Baltz, Antibiotic Resistance and antibiotic development" Harvard Academic Publishers (in press)). Current procedures use recombinant DNA techniques to isolate and manipulate secondary metabolic pathways and to express these pathways in surrogate hosts such as *S. lividans*. Heterologous expression of diverse pathways, polyketide, oligopeptide and β-lactam biosynthetic pathways, has been achieved. Furthermore novel polyketide structures have been generated through the manipulation of polyketide genes forming chimeric pathways. Recently, novel polyketide modules have been isolated from environmental sources using PCR amplification and expressed in Streptomyces to yield novel chemical structures (Strohl et al., J. Industr. Microbiol., 1991, 7:163; Kim et al., J. Bacteriol., 1995, 77:1202; Ylihonko et al., Microbiology, 1996, 142:1965).

The instant invention relates to the isolation and identification of novel genes from the *M. rosaria* pMR2 plasmid. Knowledge of the *M. rosaria* pMR2 plasmid DNA sequence, its genetic organization, and the activities associated with particular open reading frames, modules, and submodules of the gene enables the construction of novel actinomycete vectors. Modifications may be made to the DNA sequence that either alter the structure or combine functionalities contained on pMR2 with other actinomycete vector functionalities. In addition, any products resulting from post-transcriptional or post-translational modification in vivo or in vitro based on the DNA sequence information disclosed here are meant to be encompassed by the present invention.

I. Nucleic Acid Sequences

The present inventors have isolated novel genes from *M. rosaria* plasmid pMR2. Example 1 describes the cloning and sequencing of pMR2.

EXAMPLE I

Cloning and Sequencing of *M. rosaria* Plasmid pMR2

*M. rosaria* pMR2 plasmid was isolated by a modified alkaline lysis procedure (Wieser, Plasmid 1984, 12:19–36) followed by gel electrophoresis and purification of pMR2 from agarose. pMR2 DNA was digested with EcoRI and HindIII, ligated to pBluescriptIIKS and transformed into *E. coli* XL10 (Stratagene, LaJolla, Calif.) Clones containing the pMR2 fragments were identified by restriction enzyme site mapping. Two recombinants were identified containing a 6871 bp and 4129 bp HindIII to EcoRI fragment of pMR2. These were designated pSPRH813 (6871 bp insert) and pSPRH814 (4129 bp insert). The DNA sequence of the *Micromonospora rosaria* (SCC2095, NRRL3718) pMR2 plasmid was obtained by sequencing inserts of the recombinant DNA subclones pSPRH813 and pSPRH814. All sequences representing the pMR2 plasmid were fully contained in pSPRH813 and pSPRH814.

After obtaining the complete sequence of pMR2, the Gene Inspector program (Textco, Inc. West Lebanon, N.H.) and BLAST analysis (Genetics Computer Group, Program Manual for the GCG Package, Version 7, Madison, Wis.) was used to analyze the sequence of the entire *M. rosaria* pMR2 plasmid. This analysis revealed genes and sequences with BLAST homologies to database genes and to previously identified streptomycete plasmid gene homologs involved in plasmid replication, insertion and transfer. Table 1 shown below lists isolated pMR2 gene sequences and their presumed function based on BLAST homologies. Table 1 also identifies the isolated genes by SEQ ID NO. While the genes and DNA regions isolated from pMR2 share homologies with other streptomycete plasmid functions, phylogenetic analysis of the pMR2 genes and DNA regions clearly indicate that the identified pMR2 proteins and DNA regions represent novel Micromonosporacea-specific plasmid functions. Specifically these include novel genes or DNA regions involved in pMR2 replication (ORF111, rep, origin plus strand); novel site specific plasmid integration and excision (int, xis, attachment P site) regions; novel plasmid intermycelial and intramycelial transfer genes (traB, ORF101, ORF63, ORF78, ORF233, ORF52, and ORF89), and novel plasmid regulatory functions (korR, ORF111). Many of the above genes share less than 30% amino acid homology with the homologs found in the BLAST databases.

The sequences of the present invention include the specific nucleic acid sequences set forth in the Sequence Listing that forms a part of the present specification. For convenience they are designated SEQ ID NO: 1–SEQ ID NO: 15. The invention encompasses each sequence individually, as well as any combination thereof.

The gene sequences of this invention encode for both proteins and non-translated DNA regions involved in plasmid pMR2 replication, integration and excision, and conjugation. These sequences all represent novel Micromonospora-specific plasmid functions. Although the exact sequences of fourteen proteins and DNA regions are set forth in SEQ ID NOS: 2–15 and the sequence of the entire pMR2 plasmid is set forth in SEQ. ID NO: 1, the present inventors intend that their invention also relate to slight variants of these sequences. Specifically, while the specific sequences are derived from pMR2, the invention encompasses sequences that are homologous or complementary to the sequences as well as sequence- and function-conservative variants to the sequences. Sequence-conservative variants are those in which a change of one or more nucleotides in a given codon position results in no alteration in the amino acid encoded at that position. Function-conservative variants are those in which a given amino acid residue in a polypeptide has been changed without altering the overall configuration and function of the native polypeptide, including, but not limited to, replacement of an amino acid with one having similar physicochemical properties (such as, for example, acidic, basic, hydrophobic, and the like). Function-conservative variants also include any polypeptides that have the ability to elicit antibodies specific to a designated polypeptide.

In seeking to protect their invention, the present inventors have described their novel sequences in terms of specific sequences as well as those sequences sharing considerable homology to their sequences. Specifically, the inventors envision their invention to include not only the exact polynucleotide sequences as set forth in SEQ ID NOS: 1–15, but also to include polynucleotide sequences having at least about ninety percent homology to their novel isolated sequences. Preferably, the sequences of the instant invention share at least ninety-five percent homology to the sequences set forth in SEQ ID NOS: 1–15 and most preferably, share at least 98% homology to the sequences set forth in SEQ ID NOS: 1–15 including complete protein coding sequences and complements thereof.

Stringency of conditions employed in hybridizations to establish homology are dependent upon factors such as salt concentration, temperature, the presence of organic solvents, and other parameters. Stringent temperature conditions usually include temperatures in excess of about 30° C., often in excess of about 37° C., typically in excess of about 45° C., preferably in excess of about 55° C., more preferably in excess of about 65° C., and most preferably in excess of about 70° C. Stringent salt conditions will ordinarily be less than about 1000 mM, usually less than about 500 mM, more usually less than about 400 mM, preferably less than about 300 mM, more preferably less than about 200 mM, and most preferably less than about 150 mM. For example, salt concentrations of 100, 50 and 20 mM are used. The combination of the foregoing parameters, however, is more important than the measure of any single parameter. See, e.g., Wetmur et al., *J. Mol. Biol.* 31:349 (1968).

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) Adv. Appl. Math. 2:482, by the homology alignment algorithm of Needlman and Wunsch (1970) J. Mol. Biol. 48:443, by the search for similarity method of Pearson and Lipman (1988) Proc. Nat'l Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

An example of an algorithm that is suitable for determining percent sequence identity and sequence similarity is the BLAST algorithm, which is described Altschul, et al. (1990) J. Mol. Biol. 215:403–410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) Proc. Nat'l Acad. Sci. USA 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) Proc. Nat'l Acad. Sci. USA 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

TABLE 1

Gene Products and Nucleic acid regions Involved in pMR2

| Gene product or DNA region | CDA[1] | RBS[2] | SEQ ID NO: | Protein or DNA region homolog (Database No; BLAST Score) | Presumed function |
|---|---|---|---|---|---|
| attP | (59–102)* | | 2 | *Streptomyces erythrea* pSE211 attachment site (M35135,0.012) | Plasmid attachment site att P |
| origin of replication minus strand | (269–417)* | | 3 | *Streptomyces cyaneus* plasmid pSA1.1 DNA replication origin region (AB015179, 1.8e-15) | Origin of replication |
| KorR length 275aa | (2462–3286) | | 4 | *Streptomyces coelicolor* SCH69.34 probable transcriptional regulator with helix turn helix motif. (CAB45231.1, 2.2e-48) | Regulatory protein |
| ORF111 length 111aa | (3532–3867) | | 5 | No significant homologies by BLAST | Possible replication regulatory protein |
| traB length 554aa | (4408–6072) | | 6 | *Streptomyces ghanaensis* pSG5 plasmid main transfer protein (CAA56759.1, 1.8e-12) | Intramycelial transfer |

TABLE 1-continued

Gene Products and Nucleic acid regions Involved in pMR2

| Gene product or DNA region | CDA[1] | RBS[2] | SEQ ID NO: | Protein or DNA region homolog (Database No; BLAST Score) | Presumed function |
|---|---|---|---|---|---|
| ORF101 length 101aa | (6069–6374) | (6055–6059) | 7 | Deinoccoccus radiodurans conserved hypothetical protein DR2162 (AAF11706, 0.0023) | Intermycelial transfer |
| ORF63 length 62aa | (6403–6591) | (6391–6394) | 8 | Plasmid R64 pill protein, pilus formation (BAA75190, 0182) | Intermycelial transfer |
| ORF78 length 78aa | (6618–6854) | | 9 | Protein or Pseudomonas aeruginosa gacE2 plasmid protein (CAA11475,0.055) | Intermycelial transfer |
| ORF233 length 233aa | (6904–7608) | | 10 | No significant homologies by BLASLT | Intermycelial transfer |
| ORF52 length 52aa | (7605–7766) | | 11 | No significant homologies by BLAST | Intermycelial transfer |
| ORF89 length 79aa | (7770–8009) | | 12 | Plasmid pKM101 traN entry exclusion protein (U09868, 0.66) | Intermycelial transfer |
| Rep length 582aa | (8098–9846) | (8084–8088) | 13 | Ruminococcus flavefaciens Plasmid pBAW301 replication protein (AL034355, 0.17) | Replication initiator |
| Xis length 69aa | (9846–10,055) | (9834–9837) | 14 | Saccharopolyspora erythraea plasmid pSE211 excisionase (P22876, 01.027) | DNA binding, excisionase |
| Int length 387aa | (10,028–11,188) | (10,010–10,012) | 15 | Mycobacterium tuberculosis Hypothetical protein Rv2659c, Similar to phage integrase (Z80225, 6.1.e-53) | Integrase |

*CDA, RBS complement on full-length biosynthetic locus sequence
[1]CDS is then putative coding sequence
[2]RBS is the putative ribosome binding site
[3]GenBank protein database (http://www.ncbi.nih.gov/Entrez/protein.html)

II. Vectors and Transformed Hosts

The sequences of the invention may be used in any actinomycete into which the vectors of the invention are capable of integrating. For instance, the sequences of the invention may be incorporated into strains of Streptomyces, Mycobacterial, Bacilli, Micromonospora and the like. Strains such as *S. pristinaespiralis* (ATCC 256486), *S. antibioticus* (DSM 40868), *S. bikiniensis* (ATCC 11062), *S. parvulus* (ATCC 12434), *S. glauescens* (ETH 22794), *S. actuosus* (ATCC 25421), *S. coelicolor* (A3(2)), *S. ambofaciens, S. lividans, S. griseofuscus, S. limosus* are particularly useful in fermentation processes. (See also, Smokvina et al., Proceedings, 1:403–407).

Vectors that can be used in this invention include microbial plasmids, viruses, bacteriophage, integratable DNA fragments, and other vehicles which may facilitate integration of the nucleic acids into the genome of the host. Plasmids are the most commonly used form of vector but all other forms of vectors which serve an equivalent function and which are, or become, known in the art are suitable for use herein. See, e.g., Pouwels et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.

Expression of nucleic acids utilizing the vectors this invention can be carried out by conventional methods. Strains of *E. coli* and various actinomycete strains such as Streptomyces and Micromonospora strains are particularly preferred.

The invention provides a site specific integrase gene and integration site (SEQ ID NOS: 2 and 15). Use of the att/int site-specific integration functions allows for increasing a given gene dosage and for adding heterologous genes that may lead to the formation of new products, such as hybrid antibiotics. This procedure has many advantages over methods involving autonomously replicating plasmids. In particular att/int derived vectors integrate as a single copy per chromosome. Plasmids comprising the site-specific integrating functions allow integration of the gene of choice into the chromosome of actinomycetes. Integrated vectors are extremely stable which allows the gene copies to be maintained without antibiotic.

Plasmids comprising the site-specific integrating function of the invention can be used to permanently integrate copies of a heterologous gene of choice into the chromosome of many different hosts. The vectors can transform these hosts at a very high efficiency. Because the vectors do not have actinomycete origins of replication, the plasmids cannot exist as autonomously replicating vectors in actinomycete hosts. The plasmids only exist in their integrated form in these hosts. The integrated form is extremely stable which allows the gene copies to be maintained without antibiotic selective pressure. The result is highly beneficial in terms of cost, efficiency, and stability of the fermentation process.

Advantageously, the integrative vectors derived from this novel integrase also may comprise a recombinant DNA sequence coding for a desired product, including but by no means limited to an actinomycete gene. The product can be a peptide, polypeptide or protein of pharmaceutical or agri-foodstuffs importance. One can increase the copy number of the product's sequence per cell, and hence increase the levels of production of a given product. One may also create integrative vectors utilizing the att/int genes of the invention to block the biosynthesis of a metabolite, or to produce derivatives of the metabolite.

In addition to using integrating vectors to integrate genes which increase the yield of known products or generate novel products, such as hybrid antibiotics or other novel secondary metabolites, vectors can also be used to integrate antibiotic resistance genes into strains in order to carry out bioconversions with compounds to which the strain is normally sensitive. The resulting transformed hosts and methods of making the antibiotics are within the scope of the present invention.

Prokaryotic expression control sequences typically used include promoters, including those derived from the β-lactamase and lactose promoter systems [Chang et al., Nature 198:1056 (1977)], the tryptophan (trp) promoter system [Goeddel et al., Nucleic Acids Res. 8:4057 (1980)], the lambda P$_L$ promoter system [Shimatake et al., Nature 292:128 (1981)] and the tac promoter [De Boer et al., Proc. Natl. Acad. Sci. USA 292:128 (1983)]. Numerous expression vectors containing such control sequences are known in the art and available commercially.

Those skilled in the art will readily recognize that the variety of vectors which can be created utilizing the genes of the invention is virtually limitless. The only absolute requirement is that the plasmid comprise an origin of replication which functions in the host cell in which constructions are made, such as E. coli or Bacillus. No actinomycete origin of replication is required. In fact, in a specific embodiment the plasmid comprising the integrase comprises no actinomycete origin of replication. Other features, such as an antibiotic resistance gene, a multiple cloning site and cos site are useful but not required. A description of the generation and uses of cosmid shuttle vectors can be found in Rao et al., (Methods in Enzymology, 1987, 153:166198). In short, any plasmid which comprises the integrase is within the scope of this invention.

Vectors may also be created utilizing the genes of the present invention (SEQ ID NOS: 6–12) to develop conjugation vectors which allow the inter- and intramycelial transfer of plasmids between different phylogenetic classes of actinomycetes. These vectors are also useful for the manipulation of actinomycete metabolic pathways and for the study of actinomycete gene functions.

EXAMPLE II

Construction of the E. coli-actinomycete Shuttle Vector pSPRH861 and Transformation of M. carbonacea, M. halophitica and S. lividans With pSPRH861

Figure 3:
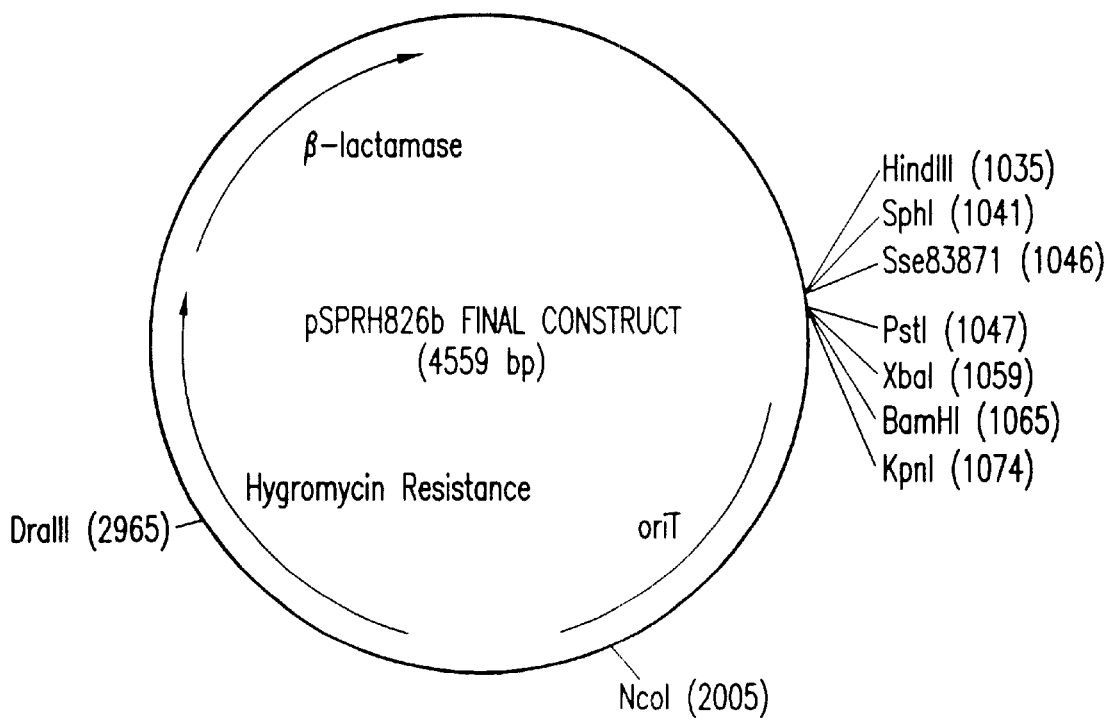
FIG. 3 Map of pSPRH826b.

PCR primers PR2000 (5'GCCTGCAGGGGCCTGACCGATGACCACTA3') and PR2001 (5'GCCTGCAGACCCGCCCGATGGACCTA3') were designed using the OLIGO Primer Analysis Software (National Biosciences, Inc. Plymouth, Minn.) to amplify a 5491 bp fragment of pMR2 containing rep, int, xis, attP, and the ds-origin regions of pMR2. PCR amplification of isolated pMR2 DNA yielded a 5.4 kb DNA fragment. The 5.4 kb fragment was ligated to pZERO-TA vector (Invitrogen Corp, Carlsbad, Calif.) to yield pSPRH855. A 5.4 kb PstI fragment from pSPRH855 was ligated to PstI digested pSPRH826b (FIG. 3.) to yield pSPRH861 (FIG. 2.).

M. carbonacea, M. halophitica and S. lividans was transformed with pSPRH861 (FIG. 2.) by conjugation from E. coli S17-1 (Mazodier et al., Journal of Bacteriology, 1989, 6, 3583–3585) to M. carbonacea, M. halophitica and S. lividans. E. coli S17-1 containing pSPR861 was grown overnight at 37° C. in LB supplemented with 100 ug/ml Ampicillin (Amp). The culture was inoculated into LB containing 100 ug/ml Amp at an 1:50 ratio and grown with shaking at 37° C. an OD600 of 0.4 to 0.5. Cells were harvested by centrifugation and washed three times with fresh LB lacking Amp. M. carbonacea, M. halophitica and S. lividans were grown separately in TSB medium at 30° C. with shaking to stationary phase. E. coli S17-1 containing pSPRH861 prepared as described above was mixed separately with M. carbonacea, M. halophitica or S. lividans in a total volume of 100 ul plated on AS1 plates using a plastic hockey spreader. Plates were incubated 15 hr at 29° C. and then overlaid with 50 ug/ml naladixic acid and 200ug/ml hygromycin for selection. Transconjugants appearing in 2–3 weeks were picked, homogenized and grown in TSB media with 50 ug/ml naladixic acid and 200 ug/ml hygromycin. Presence of pSPRH861 contained in M. carbonacea, M. halophitica and S. lividans transformants was confirmed by PCR analysis and isolation of pSPRH861 from transconjugants.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. An isolated polynucleotide comprising one or more nucleotide sequences selected from the group consisting of SEQ ID NOS: 1 and 4–15.

2. An isolated polynucleotide of claim 1, wherein said polynucleotide encodes a site-specific integrase.

3. An isolated polynucleotide of claim 1, wherein said polynucleotide encodes an excisionase.

4. An isolated polynucleotide of claim 1, wherein said polynucleotide encodes an intermycelial transfer gene.

5. An isolated polynucleotide of claim 1, wherein said polynucleotide encodes an intramycelial transfer gene.

6. An isolated polynucleotide of claim 1, wherein said polynucleotide encodes a replication regulatory protein.

7. A recombinant vector comprising one or more nucleotide sequences selected from the group consisting of SEQ ID NOS: 1 and 4–15.

8. The recombinant vector of claim 7, wherein said vector is an integration vector.

9. The recombinant vector of claim 7, wherein said vector is capable of intermycelial conjugation.

10. The recombinant vector of claim 7, wherein said vector is capable of intramycelial conjugation.

11. The recombinant vector of claim 7, wherein said vector is capable of replicating in both *Escherichia coli* and *Micromonospora* species.

12. A host cell comprising the vector of claim 7.

13. The host cell of claim 12, wherein said host is bacterial.

14. The host cell of claim 13, wherein said host is selected from the group consisting of *Micromonospora carbonacea, Micromonospora halophitica,* and *Streptymyces lividans.*

15. An isolated polynucleotide consisting of the nucleotide sequence set forth in SEQ ID NO: 2 or SEQ ID NO: 3.

16. An isolated polynucleotide of claim 15, wherein said polynucleotide encodes an origin of replication minus strand.

* * * * *

SEQUENCE LISTING

```
<160> NUMBER OF SEQ ID NOS: 15

<210> SEQ ID NO 1
<211> LENGTH: 11188
<212> TYPE: DNA
<213> ORGANISM: Micromonospora rosaria
<220> FEATURE:
<221> NAME/KEY: RBS
<222> LOCATION: (6055)..(6059)
<221> NAME/KEY: RBS
<222> LOCATION: (6391)..(6394)
<221> NAME/KEY: RBS
<222> LOCATION: (8084)..(8088)
<221> NAME/KEY: RBS
<222> LOCATION: (9834)..(9837)
<221> NAME/KEY: RBS
<222> LOCATION: (10010)..(10012)
```

-continued

```
<400> SEQUENCE: 1
tcgcacagac gttgcacgac gggcaccggc aagcccctga cctgggaaaa tgttggtgcc      60
tgaaaatcgg aaggtcggcg gttcgacccc gccctggcc acatagcctt cgccgggct      120 accaaggtcc ccaccagcgg aaacgccggt ggggatcttc ttgtatgccc tcttggcgca     180
tcgatcggcg ttgcccgtgg ttggccgtcc ttgaccgctc attgccgccg gctatcgcac     240
gtagatcgca cgccctcccc ctctgctgcc atcccgtctg ccgccgaccc acacaccgtg     300
gagcggatca gggccagggt gacaaggtgg agcaccccac tgtctgaacg accttggcac     360
cctggccctg atctgctcgg cttgcctggg tcggtggtag acgggatggc agctcccaac     420
cacccaccca ccgcaaccgt tcggcaactc catcccggag tcgtctggcc ccgccggag      480 gcacatctct aaccccgccc ccttccctac cccttgtccc ctccaccacc ctcgcccctc     540
tcctccctgg ggcctcagcg gcttcgtacg aaccgttcgg caactcgtcc tgcccgtcgg     600
tagccctcgg cctctgtggg gcctctggaa cgtcgagaac gggtgaagac gtgtccgcat     660
ggccctggtc agtccgggac tcgtcaccgg gtcccttcac ggacccaggg gtgacgcgcg     720
gggcggggcg tggtttgcgg gccggctgac tttccgcccc ggccgccgta ggcggccggg     780
gcggcggctc cgtaggagcc ggttgccgcg cccggcccg cgccgcgcgg agcgccttga      840
tctagtacag gccaattcgg caacagatca caggaagcgc tccgagtcgg cctagccagc     900
acgaacacaa cacccacccc ggccgccgcc gtccggtcgc ctcgggagtg tccgccatgc     960
cttcacgggg caatgacggt cggctgccca agtcgctccg cacgtgccgc ctgtcaacct    1020
tcaccaacta tcggcccgc ggtttcctgc cggctctgct gcttgggcct ctacctctcg    1080
ccgctcacgt cctggtcctc atcgccgaca cacgtccgcc cggacgtgca ccccacacca    1140
cgtcggcaac tcgacagacc acacccgcca accgccgctg tccttgcgta gctcccaccg    1200
ccacggatga gcactgcccg ccaggaatac gccttcgtcc caccacacgc cccgcacgtg    1260
ctctaccacc gtcgcccggt cgtcgccctg gtgctcgatg acgctggccc ctgtggcttc    1320
aagctagctt cgacggaggg cgccgggatc gggccatctc atcgcgatag ccgtgccact    1380
ggcggcgcag ctcgtcgtgt cgtccctcgg ccagcacgcg agatagcccg atgtcgtcac    1440
cagcgctcag cttcaaaagc cacaccgtgg ccgctgcctc tggcgcggct tcaccccgct    1500
cggcctccag ctgcatccga acagcccaac cagcgggcac agcaacaagg ccggcgcaga    1560
cgatcgcggc gagcgccaga agcacccagg gccatcgtcg cgccggccta cttggttgtc    1620
gtacccggtg cggtcgccaa ccttgtaggt cctccccgat gatcactgcc tgaccatacg    1680
agagggatcg aggttggcaa gaatcagatc cagtcgggct aaccgaagag ttctagaagt    1740
gctttcgcgc gacccgcaac gatgctgttc cggtggtcgc gtgcctcctg ttcaagaaac    1800
gcagcctgca tggtggtctg tcccggccat ttccgataaa gcagaccggg ttcgccgatg    1860
aaatagccct cactgagaac gttggccgct agcagcaggc cggtatcctc cgacgcggga    1920
agcgccatcc acccacccag ggcaagaagt agttggcgac gaatgcacaa ggttgcagga    1980
tgaacgggca gtcggtgccc cttgtttaac cagtgatcta ctacctgatt cttttggata    2040
ggtccatcgg gcggtcctg atgttcccaa gagattacgg acccatcagg gaggagatcc     2100
aagacacgcg acgttgtcca cccgacttcg gggctttgct ctagccggtt gatgtctctt    2160
gcgagcgttc ccggcattaa ctggtcatcc gcgtcgagaa cttttaccag ctctccggta    2220
gcccttccca acgcgacggt cctggcaacg cctggccgc ccgatcggcc tgacccgaaa     2280
ctgatcctgg gatcactggg caagtgctgc ttcagctcgc cgtcttgtcc atcttcctgg    2340
```

-continued

```
acaagccact cccagcccca cccctgcggc atctcctggg ctacgagcga ctcgtagaca    2400
tcaccgagga atgatgcaga cgacctatgc acgggagtaa tgacactcac cttgtgcgct    2460
gtcacttctt ctcccatggg tggagtttga tgccgtaaac aagctccgtt ctatccgccg    2520
ggtataccgc atcggccacc tcgacaacct tcccgtccac acccgttgaa atcttccgga    2580
tggacagaat ccaatcgccc ggttccgtcc gcaggatttc tacttcactc ggcgtgggcg    2640
gtctagcgat tacgtgatct gaaacgtggt ctacctcgac gccgattgtg aaagctggt    2700 gatgcgtacc ccccggccat ggttcgttct tgtcgtcaag aagtgcgggg tttttggcga    2760
ccgcgtcata tatcagatac gacacggaca tgctcaatgg cgcatcttcg gttttcgcgc    2820
ttgtccaata cattcgacgc aacagcttag tgcctgcctg caccttgaaa gtcgccgcaa    2880
tttcttcact ggcatcaact gtcgagtact ccgcatggaa ttgcagttga tgaacctcta    2940
ggccggtgtc gtattcagtc ccgcccttt gtcgtcgcat ctcttccggc tgatggacac     3000
gatccttctc ccactggtat cgctcgatgt tgcgccgcgt cactcgcacc tttgggctc     3060 ggacgaatgt gccccgcccc tgctcggccc gaactagccc ccattcccgt agctcccgga    3120
gggcgtttcg gacgctcgta cgagacatgc cggtccgggc cgcaagttcg ggctcactag    3180
gaagcgggga gccggcgggc agctctccgt tgacgatcct gtcgcgtagc tcctcggcta    3240
gctggacgta tcgaggtcgc cagtcacgtt cggtcacatc ggccacgcta cccctggct    3300 gtctccatgt ctgccatccc aacatgtggg cagatcaatg aggttgttga cttgtctgcc    3360
tagtcccgcc tacggtcttc ctcatcgaac ttggcagaga cgccaacaag tatccctcac    3420
cggtcgcggt gagaccacag gcaccaaagg tgcaaggagg caagagcaat ggctcttcgt    3480
ggtggtactc ggttcacggt tccgttcgag gctgtctttc cgcacggcgc ggtgttcgtg    3540
ccggactcga tcgcggaggc gcaggacttc aacgaggcga cccggcagcg gacgccgagc    3600
aaggacaagg tgaccggtga gcgggtgtgg cagtgccggg tgatggacat ggaccccgag    3660
ttgggctcgc ggtcgcgtga ggtgtcgatc aagatcctgt cgaacgtgca gccggtcccg    3720
ccggtgggtc cgttccagca ggtggagttc gagaacctga ccgtcacgcc ctacgtcggc    3780
tccaacggcc ggctcgccta ctcgttccgg gccaccggga tcgtcgcgcc gaagaccctg    3840
accgagacgc gcgggaaggc ctcctgatgg gtctgttcag tggggcaag aagaagccca     3900 aggacgtgga cgcgccgagg tcgtgcttcg agactccgcc tccgggcggg acggctcacc    3960
agcgtcgggt agcggctttc cggcgggagc acgagttgat gaacgcgatc agcaagcgtg    4020
gtcgtgagct gcggttggac cccgacaaga tcgttgacgc tcagcttgcg gctcaggagg    4080
agttgcggcg tcgggggatg gccccggagc agcttccgcc gggcgacccg gtcgacgact    4140
tcatccggta cggcatctga ggtcatgtgg cgcggggcgg tctcggccct agaccgcccc    4200 gctgcccct ccaaccttct cggcctgaaa gggcaggttc atcatgccaa cttccctgga    4260
ctggcgacgc gacgggagcg ccggagaccc ggtcccgtgc gttctctgcg gtaagccggc    4320
aatctgccgg agcccggcgg gcaagccggt gcacaaggtc tgcgctgagg cgtggatcga    4380
ccagcgcaac gccgacaagg cggtgtcgtg atgcgcgctc cgctggtcaa cttccgtcgc    4440
cttcaggtcg ccgccccgtg gcccctggtc tggacggtca cgttcttcat cctgctcgcc    4500
cggctcgtgg tcctcctcgt gggcatcgct gtcacggcgg tgcggcactg gcgggcttgg    4560
ccggctgtcg ccctggtcct gctcgccgtc gacgtgcacc gctcgcacgg ctggtggccc    4620
cacgtcctgg tccttatcgt cgtcgccgcc tcggctggca tgtggtggtg gcggtctcgg    4680
gagtccttcg aacgcctggt ggtgctgcga gggctgtcgt ggtggcggcg gctgtgggtg    4740
```

-continued

| | | | | |
|---|---|---|---|---|
| tatcggcgtc | agtggcacga | ggtcatgtcg | ctgtgtgggc | tggtgaagaa gtacgacggt | 4800 |
| ggcgagaagc | tgcccgagct | gctgtcggtg | cgctgctcgt | acgccacgga tgaagtcgtg | 4860 |
| ctgcggatgc | tcgggggca | gaacccggag | gcgtaccaca | aggcggcccg ggatctggcg | 4920 |
| tactcgttcg | gtacccggca | ctgccgcgtc | ttctccggcc | gccgccaggc accccggcc | 4980 |
| cgctccggct | ccctcgcctg | gatcctgcgc | gcgtcgacg | cgattcggtt ccgcgaccgg | 5040 |
| ccccggcagg | tgtggttggt | gctgatccgc | cgcgacccgc | tcacccgcat cgtcaagccc | 5100 |
| ctgccggtgc | cggcacgccc | ggacttcacc | gccctccccc | tcggcacgcg ggaagacctg | 5160 |
| gccgtgtact | gcctgcgtct | actcgccacg | cacgtgctga | tcggtggtgc gacgcggatg | 5220 |
| ggcaagggct | cggtcatctg | gtccctgctc | cgggctctcg | ccgccggcat ccgctcgggt | 5280 |
| ctggtgcggg | tgtgggccat | cgacccgaag | ggcgggatgg | agctgtcgat cggtcggccg | 5340 |
| ctgttctccc | gctatgtcga | tgacgactgg | acccgcatgg | ccgacatgct cgatgacgcc | 5400 |
| gtcacgagga | tgcgggctcg | tcagcgggtg | ctgcggggca | aggtgcgggt gcacaccccg | 5460 |
| accgtcgatg | aaccgctgat | tgtcatcgtc | attgacgagc | tggcgaccct gctgcgttc | 5520 |
| ctgcctgaca | gcgacattcg | tagccgcatc | gctcagtcac | tggggatgct gctctcccag | 5580 |
| ggtgccggcc | tcggcgtcct | ggtcgtcgcc | gccacccagg | accccgcaa ggaagtcgtc | 5640 |
| tccgtccgcg | acttcttccc | gacccgcatc | gccctcggcc | tgaccgaacg cggccacgtc | 5700 |
| gatctgctcc | ttggcgacgg | tgcccgcgac | cggggagcac | tggccgacca aatcccactg | 5760 |
| tcggccaagg | gcgtcgcgta | cgtcctgctt | gacggtcagc | ccgaaccggc gcgggtccgc | 5820 |
| ttctcctaca | tcagcgacga | cgtgatccgg | gagatggccg | cgaccttccc cgctcctgcc | 5880 |
| gaggtccaac | ccgaaccggt | caacaccccg | accccgaccc | cggcccggc tgcggtcaag | 5940 |
| gcccggtcga | acggcaacgg | gcggcacacc | taccggccca | ccgcgccgaa gcaggccgct | 6000 |
| ccgctgctgc | cgtcgtcgct | gcttcacgcc | ctggacctcg | acgccacccc gaacggaggc | 6060 |
| gatccccgat | gaccaccgaa | ctgcccgaga | gcaccccggc | ccggatgccc tacgccgacg | 6120 |
| aacccgacac | cacggaggaa | ccgcgccgct | tctaccggct | acgtgctccc cacgtcgaca | 6180 |
| aagcctcggt | gccggtcacc | gtccgcgtca | ccccgacgc | cgatctctac gtcgccgttg | 6240 |
| gtgccggccg | ccgccgcatg | tacctcaccc | cctccgaggc | gtgggcgctg tggcgctgcc | 6300 |
| tctccgaagc | ggtcgcctcg | acgggtgagc | cgccggagtg | gatccgcgtg cacgtcaccc | 6360 |
| ccacccaccg | ctgaccttcc | ccgcctgctt | ggagaactcg | tgatgcgtac ccatcgactg | 6420 |
| acccgacgcc | cgatccgccg | tctctgcctc | gacctggccc | acaccgaccc cgaccagacc | 6480 |
| tgccctact | gcacccccga | caacgacgcc | gccgcgatcc | tcacgccgc tctgcggcag | 6540 |
| cacgccgaga | tcgccgccga | ggacgccgaa | gcgtgggggt | gggcggcatg acctaccaac | 6600 |
| tgtggtcttg | gctcctgatg | gccgtgggcg | tcaccggcct | gtggctggcc ggaaagcgct | 6660 |
| cgtggaccgg | ctgggctgtc | ggcctcgccg | cccaggtgct | ctggctcgcg tactccctcg | 6720 |
| tgaccgagca | gtgggcttc | ctcgtctcct | gctttgtcta | cggcgcggtc tacatccgca | 6780 |
| acctgcgggc | ctggctgcgt | cccgccccgc | ccgtcacgac | cgcatcggag gtgactgctc | 6840 |
| gtgtcgacca | ctgagccggg | caccttcacg | gagcagttcg | ccaccgagta cgcccgcaac | 6900 |
| gccgtgccgg | ccatgctcaa | ggcaatcaac | tcgatcaagc | ggtacaaccg gttcgtcctg | 6960 |
| ctcggcgcgc | tgctgaccag | ctacctgcac | caagcccact | acctgtggac ccagggcgct | 7020 |
| ggtttcttcg | cctacctcgt | gcctctgatc | ttcgacgccc | cgatggtgtc catgctgacc | 7080 |
| gtcgtccgca | cctccggcat | cgctcgtgat | gccaagcggg | gagcgttggt cgtgttcgcc | 7140 |

-continued

```
gccgccgcca tgttgtcggc caccatcaac ttcgcgtccc ccggcagcct cggcctacgt    7200
ctggtcttcg ccctggtcgt cgtcctcgtc atcggcgtcg aactcgtcgc cggacgcatc    7260
cgacccgact tcgccgccat cgaagccgaa gcagccgccc tcctcaccgc tgcccgcgac    7320
ctggccgcga agaaccagcg gaccagcgaa cccaccgaca ccccggctac ggacccggac    7380
ccggacccgt tcaaggcaac cgccccgggg cctgcgcctg agtccgtcga cccggacccg    7440
atcgacctgc ccatcgaccc ggcacctgtc tacgtcccac cggcacccgt aatcgtcccg    7500
gccccggccc ggccggcccc gacccggctg gtgtccacca ccgtccagca gcccgccacc    7560
atccccgccc ggatgaacgg gcagatcgtc tcgggagtga tccgatgaac tgctacacca    7620
cccaggggcg taagtcctcc tacgtctacc aggtcggcag cgacttcgtg ggcttctgca    7680
ccggctgcgg gtggaccgtc accaaagtcg gccacgcccc ggccctgatg gcggccagcg    7740
accacgcaca gaactgctgg gcctgaccga tgaccactaa cacgggcaac cgcctgatcc    7800
gccgtctgta cgagcgcgcc accggccgcc cctggctgac cgtccgcagc gtcaccgacg    7860
agttcggccc gaccccggt gcccgctacg ccgatctcct cgaccagtac accgacgccg    7920
aactcctggc cttcggtgat ctcatcctcg ccgcctgcat cgccgccgac cacaaccccg    7980
acccggtccc ggaccggcg accgctgac cccgccccg gttggcccac cgccctcacc    8040
ccggagcggt gggccagcca cccccatccc tcgcacacgt cctggaggtg aaccaccgtg    8100
atcgccccga ccctgcccgg cctcaccccc gacaccaccc ccgccgaacc gacctcggcc    8160
ggggctgccc cgccggcggc tggctcccgt gccgcacgcc tcgccctgcc gatgtcccgg    8220
caggtgttga aggagatggc cgctgagtat ggcgtgtgcc tgcgcccggt caccctgcgc    8280
cggactgacc tgagcaccgg tcagaccgaa gtgatcgacc tgccgtgtgg caccacgcgcg   8340
gaagacaagt gctccccgtg cgcgaagcgt gcccgccggc tgcgtcagac ccagatccgc    8400
gagggctggc accgcaccga cgaacccaat cctttcgccc cctggcccgc cagcgaggaa    8460
cagcgcgact tggtcatgct gcgggcgcac ctggaattcg cccgcgagga agcacagcgc    8520
tccgcacagt tcgaccaggt gcccggcatc gatcaggcca tcgccgaggt agaggaagcc    8580
atcgccgccg agggcctacg cggacaggtc gccccacccc acgacgggga aggctccgca    8640
ggtggccggc gcaagcggtc gaccaaacgg cgtcaggaca cccccgacct gccccgtaag    8700
aaggtcgagc cgcgcaccgt gggacaggtc tataccgccc cggacggcac ccagcaccgg    8760
ccgtccatgt ggctgtcgct caccctcgac tcctacggcc gcgtcctgcc tgacggcacg    8820
cccgtcgacc cggacagcta cgactaccgg cgggccgcct gggacgccgt gcacttcgct    8880
cggctgctca tcggttctg gcagaacctg cgccgctgcg tcggctggaa cgtccagtac    8940
gccggctgcg tcgagcccca acgacgcctc gccccgcacg cccacttcgc catccggggc    9000
accatccccc gcgccgtgct gcggcaggtc gccgccgcca cctatcacca ggtgtggtgg    9060
ccgccggctg atgagctggt gtactcgctg gatcggctgc cggtgtggga caacgacgct    9120
gacgcctggg ttgaccccga cacccgcgag ccgctgacga cgtgggctga cgccttggac    9180
ctgctcgacg ccgaccccga cgcgcaaccc gtacacgtcg tccgcttcgg ccgccaagtc    9240
cacgccgagg gcgtcacccc cggcaccgtg cacgccgaac ggaccatcgg ctacatcacg    9300
aagtacatca ccaagagcgc cgccgactgc acaaggccg agacgaaccg gcagcgcaac    9360
cacctggaac ggctctggca acagctccgc gtcacgccgt gcaacgagcg gtgcgccaac    9420
tggctgcttt acgcgtccca gccgaagaag gcacacggcc gcctgcaagc ggggcgctgc    9480
aagggaaagg tccaccagcg ggccaccctc ggcatcggtg ggcgccgcat cctcgtctcg    9540
```

-continued

```
cgcgactggt ccggaaagac cctcgccgac caccgcgccg acgcccgcgc ctgggtccgc    9600
cggctcctgg gcgtcagcac cggggcagac gatgccgacc ccgtcgacca gggcgacgcg    9660
cccgtctacg cctgggaaat ggctcggccg gatgaccccg acatcccacc cctgcaacac    9720
cggatgcttc gggcactgtc ccaacgcgcc caatggaagg ccgccctacg cgctgcccag    9780
gatcgagcgg cggccagctc gtcagacgtc tcggcagtcc cctcggaccg gaaggagtcg    9840
cggtagtgga acggctattg acggtggctc aggccgccga tcatctcggg acgacggagc    9900
gtttcccgcg tcggctgatc gctgagcggc gaatccggtt cgtcaagctc ggctctcacg    9960
tccgcattcc cgaaagcgcc ttggctgagt tcatcgctgc cggcgtcgtg aaccggtga    10020 ccctgtcatg gtcggacggg aaggcggtgg cctgatgggt agtcgccgcc agttcggttc    10080
ggttcgcaag ctgccgtcgg ggcgttttca ggcgtcgttc cttccgcctg gtggtgggcc    10140
tcgacagaac gcgccacaca cgttcaagac gaagactgat gctcatcggt ggctcacccg    10200
cgttgaggcc gacatctcgc ggggtacctg gttggatgac cgggcggccg gtgagacctt    10260
cggtaactac gcacgggcca tcctgcggga cagcccgaag atcggtgtcc gctggcggga    10320
gacctgcgaa cggaacttga ggcttcacct ggtgccgctg gtcacggtgc cctgcgggga    10380
ggtgacggcc agccgggtcc gcgaatggca cgctgctgcc ctacgggct ccggtggccg    10440 cacatccatc tctcagtcgt accggttcct gcggatggtc atgaacaccg ctgtccgtga    10500
gggcatcatc gcccggtcac cctgccagat ccccggagcg ggcaccgtcc gtgctgcgga    10560
acggccggtt gccaccccgg ctcaggtcgt cgccctggtc gaggccatca cccgcgcta    10620 ccggacggcg gtcctgatcg cggcctggtg cggcctacgc cggggagaga tcgcaggact    10680
ccgggtcgca gacgtggacc tgaccgaaca caccatcacc gtccgcaaag ccagggtcga    10740
accgctgcac gacagggga aggcgtttga caaggatccc aagtccgagg cgggcaagcg    10800
aaccatcgcc atccctcccc acgtcgtacc cgtgatccgc ctgcacctcg acgagttcgc    10860
cgggaaggat cgcctgttcg tcagccgcga cggatcaccc ctgcgcggcg acaccctgta    10920
ccaggcgttc gtacgcgctc ggggaaaggt cggactcgac accctcacct tccacgacct    10980
gcggcacacc ggtcagaccc tcgccgcgca gaccggggcg accttggccg acctgatgaa    11040
gcggctcggg cactcgtcca tggctgcggc tcgccggtac ctcccacgccg ttgacggtcg    11100 tgaccgggag atcgccaaag ccctttccga gctggcggcg cacggtgatg tcgcacggct    11160
gccccggcac atcacgatgc ggagttag                                       11188

<210> SEQ ID NO 2
<211> LENGTH: 44
<212> TYPE: DNA
<213> ORGANISM: Micromonospora rosaria

<400> SEQUENCE: 2
cctgaaaatc ggaaggtcgg cggttcgacc ccgcccctgg ccac                       44

<210> SEQ ID NO 3
<211> LENGTH: 149
<212> TYPE: DNA
<213> ORGANISM: Micromonospora rosaria

<400> SEQUENCE: 3
ccatcccgtc tgccgccgac ccacacaccg tggagcggat cagggccagg gtgacaaggt     60
ggagcacccc actgtctgaa cgaccttggc accctggccc tgatctgctc ggcttgcctg   120
ggtcggtggt agacgggatg gcagctccc                                      149
```

```
<210> SEQ ID NO 4
<211> LENGTH: 825
<212> TYPE: DNA
<213> ORGANISM: Micromonospora rosaria

<400> SEQUENCE: 4
tcacttcttc tcccatgggt ggagtttgat gccgtaaaca agctccgttc tatccgccgg     60
gtataccgca tcggccacct cgacaacctt cccgtccaca cccgttgaaa tcttccggat    120
ggacagaatc caatcgcccg gttccgtccg caggatttct acttcactcg gcgtgggcgg    180
tctagcgatt acgtgatctg aaacgtggtc tacctcgacg ccgattgtgg aaagctggtg    240
atgcgtaccc cccggccatg gttcgttctt gtcgtcaaga agtgcggggt ttttggcgac    300
cgcgtcatat atcagatacg acacggacat gctcaatggc gcatcttcgg ttttcgcgct    360
tgtccaatac attcgacgca acagcttagt gcctgcctgc accttgaaag tcgccgcaat    420
ttcttcactg gcatcaactg tcgagtactc gcatggaat tgcagttgat gaacctctag    480
gccggtgtcg tattcagtcc cgccttttg tcgtcgcatc tcttccggct gatggacacg    540
atccttctcc cactggtatc gctcgatgtt gcgccgcgtc actcgcacct ttgggctcg    600 gacgaatgtg ccccgcccct gctcggcccg aactagcccc cattcccgta gctcccggag    660
ggcgtttcgg acgctcgtac gagacatgcc ggtccgggcc gcaagttcgg gctcactagg    720
aagcggggag ccggcgggca gctctccgtt gacgatcctg tcgcgtagct cctcggctag    780
ctggacgtat cgaggtcgcc agtcacgttc ggtcacatcg gccac                   825

<210> SEQ ID NO 5
<211> LENGTH: 336
<212> TYPE: DNA
<213> ORGANISM: Micromonospora rosaria

<400> SEQUENCE: 5
gtgttcgtgc cggactcgat cgcggaggcg caggacttca acgaggcgac ccggcagcgg     60
acgccgagca aggacaaggt gaccggtgag cgggtgtggc agtgccgggt gatggacatg    120
gaccccgagt tgggctcgcg gtcgcgtgag gtgtcgatca agatcctgtc gaacgtgcag    180
ccggtcccgc cggtgggtcc gttccagcag gtggagttcg agaacctgac cgtcacgccc    240
tacgtcggct ccaacggccg gctcgcctac tcgttccggg ccaccgggat cgtcgcgccg    300
aagaccctga ccgagacgcg cgggaaggcc tcctga                              336

<210> SEQ ID NO 6
<211> LENGTH: 1665
<212> TYPE: DNA
<213> ORGANISM: Micromonospora rosaria

<400> SEQUENCE: 6
gtgatgcgcg ctccgctggt caacttccgt cgccttcagg tcgccgcccc gtggcccctg     60
gtctggacgg tcacgttctt catcctgctc gcccggctcg tggtcctcct cgtgggcatc    120
gctgtcacgg cggtgcggca ctggcgggct tggccggctg tcgccctggt cctgctcgcc    180
gtcgacgtgc accgctcgca cggctggtgg ccccacgtcc tggtccttat cgtcgtcgcc    240
gcctcggctg gcatgtggtg gtggcggtct cgggagtcct tcgaacgcct ggtggtgctg    300
cgagggctgt cgtggtggcg gcggctgtgg gtgtatcggc gtcagtggca cgaggtcatg    360
tcgctgtgtg ggctggtgaa gaagtacgac ggtggcgaga gctgcccga gctgctgtcg    420 gtgcgctgct cgtacgccac ggatgaagtc gtgctgcgga tgcctcgggg gcagaacccg    480
```

-continued

```
gaggcgtacc acaaggcggc ccgggatctg gcgtactcgt tcggtacccg gcactgccgc        540
gtcttctccg gccgccgcca ggcaccccg gcccgctccg gctccctcgc ctggatcctg         600
cgccgcgtcg acgcgattcg gttccgcgac cggccccggc aggtgtggtt ggtgctgatc        660
cgccgcgacc cgctcacccg catcgtcaag ccctgccgg tgccggcacg cccggacttc         720
accgccctcc cctcggcac gcgggaagac ctggccgtgt actgcctgcg tctactcgcc        780
acgcacgtgc tgatcggtgg tgcgacgcgg atgggcaagg gctcggtcat ctggtccctg        840
ctccgggctc tcgccgccgg catccgctcg ggtctggtgc gggtgtgggc catcgacccg        900
aagggcggga tggagctgtc gatcggtcgg ccgctgttct cccgctatgt cgatgacgac        960
tggacccgca tggccgacat gctcgatgac gccgtcacga ggatgcgggc tcgtcagcgg       1020
gtgctgcggg gcaaggtgcg ggtgcacacc ccgaccgtcg atgaaccgct gattgtcatc       1080
gtcattgacg agctggcgac cctgctggcg ttcctgcctg acagcgacat tcgtagccgc       1140
atcgctcagt cactggggat gctgctctcc cagggtgccg gcctcggcgt cctggtcgtc       1200
gccgccaccc aggaccccg caaggaagtc gtctccgtcc gcgacttctt cccgacccgc        1260
atcgccctcg gcctgaccga acgcggccac gtcgatctgc tccttggcga cggtgcccgc       1320
gaccggggag cactggccga ccaaatccca ctgtcggcca agggcgtcgc gtacgtcctg       1380
cttgacggtc agcccgaacc ggcgcgggtc cgcttctcct acatcagcga cgacgtgatc       1440
cgggagatgg ccgcgacctt ccccgctcct gccgaggtcc aacccgaacc ggtcaacacc       1500
ccgaccccga cccggcccc ggctgcggtc aaggcccggt cgaacggcaa cgggcggcac        1560
acctaccggc ccaccgcgcc gaagcaggcc gctccgctgc tgccgtcgtc gctgcttcac       1620
gccctggacc tcgacgccac ccgaacggga ggcgatcccc gatga                      1665
```

<210> SEQ ID NO 7
<211> LENGTH: 306
<212> TYPE: DNA
<213> ORGANISM: Micromonospora rosaria

<400> SEQUENCE: 7

```
atgaccaccg aactgcccga gagcaccccg gcccggatgc cctacgccga cgaacccgac         60
accacggagg aaccgcgccg cttctaccgg ctacgtgctc cccacgtcga caaagcctcg        120
gtgccggtca ccgtccgcgt caccccgac gccgatctct acgtcgccgt tggtgccggc        180
cgccgccgca tgtacctcac cccctccgag gcgtgggcgc tgtggcgctg cctctccgaa       240
gcggtcgcct cgacgggtga gccgccggag tggatccgcg tgcacgtcac ccccacccac       300
cgctga                                                                    306
```

<210> SEQ ID NO 8
<211> LENGTH: 189
<212> TYPE: DNA
<213> ORGANISM: Micromonospora rosaria

<400> SEQUENCE: 8

```
atgcgtaccc atcgactgac ccgacgcccg atccgccgtc tctgcctcga cctggcccac         60
accgaccccg accagacctg cccctactgc acccccgaca cgacgccgc cgcgatcctc        120 acggccgctc tgcggcagca cgccgagatc gccgccgagg acgccgaagc gtggggggtgg      180 gcggcatga                                                                 189
```

<210> SEQ ID NO 9
<211> LENGTH: 237
<212> TYPE: DNA
<213> ORGANISM: Micromonospora rosaria

<400> SEQUENCE: 9

| | | | | | |
|---|---|---|---|---|---|
| atggccgtgg | gcgtcaccgg | cctgtggctg | gccggaaagc | gctcgtggac | cggctgggct | 60 |
| gtcggcctcg | ccgcccaggt | gctctggctc | gcgtactccc | tcgtgaccga | gcagtggggc | 120 |
| ttcctcgtct | cctgctttgt | ctacggcgcg | gtctacatcc | gcaacctgcg | ggcctggctg | 180 |
| cgtcccgccc | cgcccgtcac | gaccgcatcg | gaggtgactg | ctcgtgtcga | ccactga | 237 |

<210> SEQ ID NO 10
<211> LENGTH: 705
<212> TYPE: DNA
<213> ORGANISM: Micromonospora rosaria

<400> SEQUENCE: 10

| | | | | | |
|---|---|---|---|---|---|
| gtgccggcca | tgctcaaggc | aatcaactcg | atcaagcggt | acaaccggtt | cgtcctgctc | 60 |
| ggcgcgctgc | tgaccagcta | cctgcaccaa | gcccactacc | tgtggaccca | gggcgctggt | 120 |
| ttcttcgcct | acctcgtgcc | tctgatcttc | gacgccgcga | tggtgtccat | gctgaccgtc | 180 |
| gtccgcacct | ccggcatcgc | tcgtgatgcc | aagcggggag | cgttggtcgt | gttcgccgcc | 240 |
| gccgccatgt | tgtcggccac | catcaacttc | gcgtcccccg | gcagcctcgg | cctacgtctg | 300 |
| gtcttcgccc | tggtcgtcgt | cctcgtcatc | ggcgtcgaac | tcgtcgccgg | acgcatccga | 360 |
| cccgacttcg | ccgccatcga | agccgaagca | gccgccctcc | tcaccgctgc | ccgcgacctg | 420 |
| gccgcgaaga | accagcggac | cagcgaaccc | accgacaccc | cggctacgga | cccggacccg | 480 |
| gacccggtca | aggcaaccgc | cccggggcct | gcgcctgagt | ccgtcgaccc | ggacccgatc | 540 |
| gacctgccca | tcgacccggc | acctgtctac | gtcccaccgg | cacccgtaat | cgtcccggcc | 600 |
| ccggcccggc | cggccccgac | ccggctggtg | tccaccaccg | tccagcagcc | cgccaccatc | 660 |
| cccgcccgga | tgaacgggca | gatcgtctcg | ggagtgatcc | gatga | | 705 |

<210> SEQ ID NO 11
<211> LENGTH: 162
<212> TYPE: DNA
<213> ORGANISM: Micromonospora rosaria

<400> SEQUENCE: 11

| | | | | | |
|---|---|---|---|---|---|
| atgaactgct | acaccaccca | ggggcgtaag | tcctcctacg | tctaccaggt | cggcagcgac | 60 |
| ttcgtgggct | tctgcaccgg | ctgcgggtgg | accgtcacca | aagtcggcca | cgccccggcc | 120 |
| ctgatggcgg | ccagcgacca | cgcacagaac | tgctgggcct | ga | | 162 |

<210> SEQ ID NO 12
<211> LENGTH: 240
<212> TYPE: DNA
<213> ORGANISM: Micromonospora rosaria

<400> SEQUENCE: 12

| | | | | | |
|---|---|---|---|---|---|
| atgaccacta | acacgggcaa | ccgcctgatc | cgccgtctgt | acgagcgcgc | caccggccgc | 60 |
| ccctggctga | ccgtccgcag | cgtcaccgac | gagttcggcc | cgaccccgg | tgccgctac | 120 |
| gccgatctcc | tcgaccagta | caccgacgcc | gaactcctgg | ccttcggtga | tctcatcctc | 180 |
| gccgcctgca | tcgccgccga | ccacaacccc | gaccggtcc | cggacccggc | gacccgctga | 240 |

<210> SEQ ID NO 13
<211> LENGTH: 1749
<212> TYPE: DNA
<213> ORGANISM: Micromonospora rosaria

<400> SEQUENCE: 13

| | | | | | |
|---|---|---|---|---|---|
| gtgatcgccc | cgaccctgcc | cggcctcacc | cccgacacca | ccccgccga | accgacctcg | 60 |
| gccggggctg | ccccgccggc | ggctggctcc | cgtgccgcac | gcctcgccct | gccgatgtcc | 120 |
| cggcaggtgt | tgaaggagat | ggccgctgag | tatgcgtgt | gcctgcgccc | ggtcaccctg | 180 |
| cgccggactg | acctgagcac | cggtcagacc | gaagtgatcg | acctgccgtg | tggcaccacg | 240 |
| cgggaagaca | agtgctcccc | gtgcgcgaag | cgtgcccgcc | ggctgcgtca | gacccagatc | 300 |
| cgcgagggct | ggcaccgcac | cgacgaaccc | aatcctttcg | cccctggcc | cgccagcgag | 360 |
| gaacagcgcg | acttggtcat | gctgcgggcg | cacctggaat | tcgcccgcga | ggaagcacag | 420 |
| cgctccgcac | agttcgacca | ggtgcccggc | atcgatcagg | ccatcgccga | ggtagaggaa | 480 |
| gccatcgccg | ccgagggcct | acgcggacag | gtcgccccac | ccacgacgg | ggaaggctcc | 540 |
| gcaggtggcc | ggcgcaagcg | gtcgaccaaa | cggcgtcagg | acaccccga | cctgccccgt | 600 |
| aagaaggtcg | agccgcgcac | cgtgggacag | gtctataccg | ccccggacgg | cacccagcac | 660 |
| cggccgtcca | tgtggctgtc | gctcaccctc | gactcctacg | gccgcgtcct | gcctgacggc | 720 |
| acgcccgtcg | acccggacag | ctacgactac | cggcgggccg | cctgggacgc | cgtgcacttc | 780 |
| gctcggctgc | tcgatcggtt | ctggcagaac | ctgccgcgct | gcgtcggctg | gaacgtccag | 840 |
| tacgccggct | gcgtcgagcc | ccaacgacgc | ctcgccccgc | acgcccactt | cgccatccgg | 900 |
| ggcaccatcc | cccgcgccgt | gctgcggcag | gtcgccgccg | ccacctatca | ccaggtgtgg | 960 |
| tggccgccgg | ctgatgagct | ggtgtactcg | ctggatcggc | tgccggtgtg | ggacaacgac | 1020 |
| gctgacgcct | gggttgaccc | cgacaccgc | gagccgctga | cgacgtgggc | tgacgccttg | 1080 |
| gacctgctcg | acgccgaccc | cgacgcgcaa | cccgtacacg | tcgtccgctt | cggccgccaa | 1140 |
| gtccacgccg | agggcgtcac | ccccggcacc | gtgcacgccg | aacggaccat | cggctacatc | 1200 |
| acgaagtaca | tcaccaagag | cgccgccgac | tgccacaagg | ccgagacgaa | ccggcagcgc | 1260 |
| aaccacctgg | aacggctctg | gcaacagctc | cgcgtcacgc | cgtgcaacga | gcggtgcgcc | 1320 |
| aactggctgc | tttacggcgt | ccagccgaag | aaggcacacg | gccgcctgca | agcggggcgc | 1380 |
| tgcaagggaa | aggtccacca | gcgggccacc | ctcggcatcg | gtgggcgccg | catcctcgtc | 1440 |
| tcgcgcgact | ggtccggaaa | gaccctcgcc | gaccaccgc | ccgacgcccg | cgcctgggtc | 1500 |
| cgccggctcc | tgggcgtcag | caccggggca | gacgatgccg | accccgtcga | ccagggcgac | 1560 |
| gcgcccgtct | acgcctggga | aatggctcgg | ccggatgacc | ccgacatccc | accctgcaa | 1620 |
| caccggatgc | ttcgggcact | gtcccaacgc | gcccaatgga | aggccgccct | acgcgctgcc | 1680 |
| caggatcgag | cggcggccag | ctcgtcagac | gtctcggcag | tccctcgga | ccggaaggag | 1740 |
| tcgcggtag | | | | | | 1749 |

<210> SEQ ID NO 14
<211> LENGTH: 210
<212> TYPE: DNA
<213> ORGANISM: Micromonospora rosaria

<400> SEQUENCE: 14

| | | | | | |
|---|---|---|---|---|---|
| gtggaacggc | tattgacggt | ggctcaggcc | gccgatcatc | tcgggacgac | ggagcgtttc | 60 |
| ccgcgtcggc | tgatcgctga | gcggcgaatc | cggttcgtca | agctcggctc | tcacgtccgc | 120 |

-continued

```
attcccgaaa gcgccttggc tgagttcatc gctgccggcg tcgtggaacc ggtgaccctg      180
tcatggtcgg acgggaaggc ggtggcctga                                       210

<210> SEQ ID NO 15
<211> LENGTH: 1161
<212> TYPE: DNA
<213> ORGANISM: Micromonospora rosaria

<400> SEQUENCE: 15
atggtcggac gggaaggcgg tggcctgatg ggtagtcgcc gccagttcgg ttcggttcgc       60
aagctgccgt cggggcgttt tcaggcgtcg ttccttccgc ctggtggtgg gcctcgacag      120
aacgcgccac acacgttcaa gacgaagact gatgctcatc ggtggctcac ccgcgttgag      180
gccgacatct cgcggggtac ctggttggat gaccgggcgg ccggtgagac cttcggtaac      240
tacgcacggg ccatcctgcg ggacagcccg aagatcggtg tccgctggcg ggagacctgc      300
gaacggaact tgaggcttca cctggtgccg ctggtcacgg tgcccctgcg ggaggtgacg      360
gccagccggg tccgcgaatg gcacgctgct gccctacggg gctccggtgg ccgcacatcc      420
atctctcagt cgtaccggtt cctgcggatg gtcatgaaca ccgctgtccg tgagggcatc      480
atcgcccggt caccctgcca gatccccgga gcgggcaccg tccgtgctgc ggaacggccg      540
gttgccaccc cggctcaggt cgtcgccctg gtcgaggcca tcaaccgcg ctaccggacg       600 gcggtcctga tcgcggcctg gtgcggccta cgccggggag agatcgcagg actccgggtc      660
gcagacgtgg acctgaccga acacaccatc accgtccgca aagccagggt cgaaccgctg      720
cacgacaggg ggaaggcgtt tgacaaggat cccaagtccg aggcgggcaa gcgaaccatc      780
gccatccctc cccacgtcgt acccgtgatc cgcctgcacc tcgacgagtt cgccgggaag      840
gatcgcctgt tcgtcagccg cgacggatca ccctgcgcg gcgacaccct gtaccaggcg       900
ttcgtacgcg ctcggggaaa ggtcggactc gacaccctca ccttccacga cctgcggcac      960
accggtcaga ccctcgccgc gcagaccggg gcgaccttgg ccgacctgat gaagcggctc     1020
gggcactcgt ccatggctgc ggctcgccgg tacctccacg ccgttgacgg tcgtgaccgg     1080
gagatcgcca aagcccttc cgagctggcg gcgcacggtg atgtcgcacg gctgccccgg     1140
cacatcacga tgcggagtta g                                               1161
```